(12) United States Patent
Heckerman et al.

(10) Patent No.: US 10,795,969 B2
(45) Date of Patent: Oct. 6, 2020

(54) REMOTE LIFE SCIENCE LABORATORIES AND STORAGE FACILITIES

(71) Applicant: Microsoft Technology Licensing, LLC, Redmond, WA (US)

(72) Inventors: David E. Heckerman, Santa Monica, CA (US); David H. Shute, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 878 days.

(21) Appl. No.: 15/160,741

(22) Filed: May 20, 2016

(65) Prior Publication Data

US 2017/0337337 A1 Nov. 23, 2017

(51) Int. Cl.
*G05B 21/00* (2006.01)
*G06F 19/00* (2018.01)
*G16H 40/20* (2018.01)

(52) U.S. Cl.
CPC ......... *G06F 19/3418* (2013.01); *G16H 40/20* (2018.01); *Y02A 90/22* (2018.01); *Y02A 90/26* (2018.01)

(58) Field of Classification Search
CPC ............ G05B 2219/2614; G05B 15/00; G05B 19/058
USPC .................................................. 700/266, 276
See application file for complete search history.

(56) References Cited

U.S. PATENT DOCUMENTS

| 9,250,254 | B2 | 2/2016 | Bates et al. |
| 2003/0171876 | A1 | 9/2003 | Markowitz et al. |
| 2005/0069861 | A1* | 3/2005 | Zimmermann .......... A01N 1/02 |
| | | | 435/1.1 |
| 2014/0164516 | A1 | 6/2014 | Maltbie et al. |
| 2015/0242395 | A1 | 8/2015 | Hodak |
| 2015/0376692 | A1 | 12/2015 | Esfandyarpour et al. |

FOREIGN PATENT DOCUMENTS

WO    WO2013107463 A1    7/2013

OTHER PUBLICATIONS

"ECL Emerald Cloud Lab", Published on: Jul. 8, 2014, Available at: http://emeraldcloudlab.com/how-it-works#how-it-works, 5 pgs.
(Continued)

*Primary Examiner* — Natalia Levkovich
(74) *Attorney, Agent, or Firm* — Schwegman Lundberg & Woessner, P.A.

(57) ABSTRACT

An automated life science laboratory or a storage facility for biological specimens may be located together with or in close proximity to a data center. The location of the data center, the automated life science laboratory, and the storage facility may be a location in which land and/or electricity are less expensive than locations where the biological specimens are collected. The automated life science laboratory may have a high-capacity data connection to the data center. The life science laboratory, storage facility, and the data center may share a connection to the electrical grid, an HVAC system, and/or a security perimeter. A biological specimen may be removed from storage at the storage facility, process by one or more biotechnology protocols at the automated life science laboratory, and data from the processing may be stored in the data center.

6 Claims, 4 Drawing Sheets

(56) References Cited

OTHER PUBLICATIONS

"Freezer PRO", Retrieved on: Feb. 26, 2016, Available at: https://www.freezerpro.com/biobank-software, 5 pgs.
Gostev, et al., "SAIL—A Software System for Sample and Phenotype Availability Across Biobanks and Cohorts", Bioinformatics, 2011, vol. 27 (4), Dec. 17, 2010, pp. 589-591.
Malm, et al., "Semi-Automated Biobank Sample Processing with a 384 High Density Sample Tube Robot used in Cancer and Cardiovascular Studies", Clinical and Translational Medicine, Dec. 2015, vol. 4 (1), pp. 1-8.
Prokosch, et al., "IT Infrastructure Components for Biobanking", Applied Clinical Informatics, Nov. 24, 2010, vol. 1 (4), pp. 419-429.

\* cited by examiner

REMOTE LIFE SCIENCE LABORATORIES AND STORAGE FACILITIES

BACKGROUND

Due to the increased usage of the Internet in recent decades, there has been an increase in the number and size of data centers. A data center is a facility used to house computer systems and associated components, such as telecommunications and storage systems. Site selection for data centers take into account the availability and price of power, land prices, climatic conditions, geological risks, and other factors. It is generally preferable to locate a data center in a place where power is relatively inexpensive to reduce the cost of the computers and where the climate is cool to assist with dissipating heat generated by the computers. Large data centers may include buildings that cover several hundred thousand square feet and consume as much electricity as a small town. Thus, significant time and energy is spent identifying suitable locations for data centers. The factors that make a particular location well suited for a data center may also make the same location suitable for siting other facilities.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

An automated life science laboratory may be situated at the same location as a data center. The automated life science laboratory can receive instructions electronically, such as over the Internet, and implement those instructions using automated machines and robotics to perform biotechnology protocols like DNA sequencing. A storage facility for biological specimens may also be situated at the same location as a data center. In an implementation, both the automated life science laboratory and the storage facility are located together with the data center. The storage facility may include various refrigerators, freezers, and other storage areas for storing a number of biological specimens. Many of the factors that are considered when selecting a site for a data center are also appropriate for determining where to locate an automated life science laboratory or a storage facility. Lower costs for land and low-cost electricity are advantageous for automated life science laboratories and storage facilities as well as for data centers. Physical security put in place for the data center may also be used to protect biological specimens and equipment. Electrical and cooling systems implemented for the data center may be shared with the automated life science laboratory or storage facility.

Physical proximity between the automated life science laboratory and the data center also allows for a direct high-speed data connection. Large volumes of data created by the life science laboratory, such as data from DNA sequencers, may be moved to the data center quickly and securely. The data center may also be used to perform analytics on data generated by the life science laboratory. Thus, once biological specimens are delivered to the storage facility, many types of biotechnology protocols may be implemented by the automated life science laboratory and many types of data manipulations may be implemented by the data center.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

As adoption of personalized medicine increases, there will be a concurrent strong need to store and analyze biological specimens from patients. Currently biological specimens are often stored on-site at a hospital or medical center, frequently in an urban location where space is at a premium and electricity prices may be relatively high compared to other regions. Once collected, biological specimens may be analyzed immediately or stored for a period of time and then analyzed later when relevant technology improves or when the condition of a patient changes. Analysis of the biological specimens is performed by a biotechnology protocol and is often conducted manually at the same location where the biological specimens are collected and stored. Thus, the equipment and laboratory space for performing the biotechnology protocols are often located in a hospital or medical center where space and electricity are relatively expensive. However, there is no fundamental requirement that storage and analysis of biological specimens be performed in close geographic proximity to the location where the biological specimen was obtained. Many biotechnology protocols for analyzing biological specimens have been largely or entirely automated through the use of microfluidics, robotics, and other technologies. Thus, the doctor or other clinician involved in obtaining a biological specimen from a patient may send the biological specimen away for automated analysis by one or more biotechnology protocols.

Many businesses have gone to great lengths to identify and build data centers in areas where land and electricity are relatively inexpensive. Many of the reasons that make a given location a good place to site a data center also make the same location a good place for an automated life science laboratory and/or a storage facility for biological specimens. Affordable space and electricity is a benefit for storage of biological specimens and operation of equipment that performs biotechnology protocols. Refrigerators and freezers to store biological specimens require electricity and a cool climate will reduce the amount of electricity needed to maintain the low temperatures. The locations for siting a data center are also often evaluated for geologic stability and low risk of natural disasters. The work that has gone in to identifying locations for data centers and the characteristics of those locations can be beneficially used for placing automated life science laboratories and storage facilities.

Figure 1:
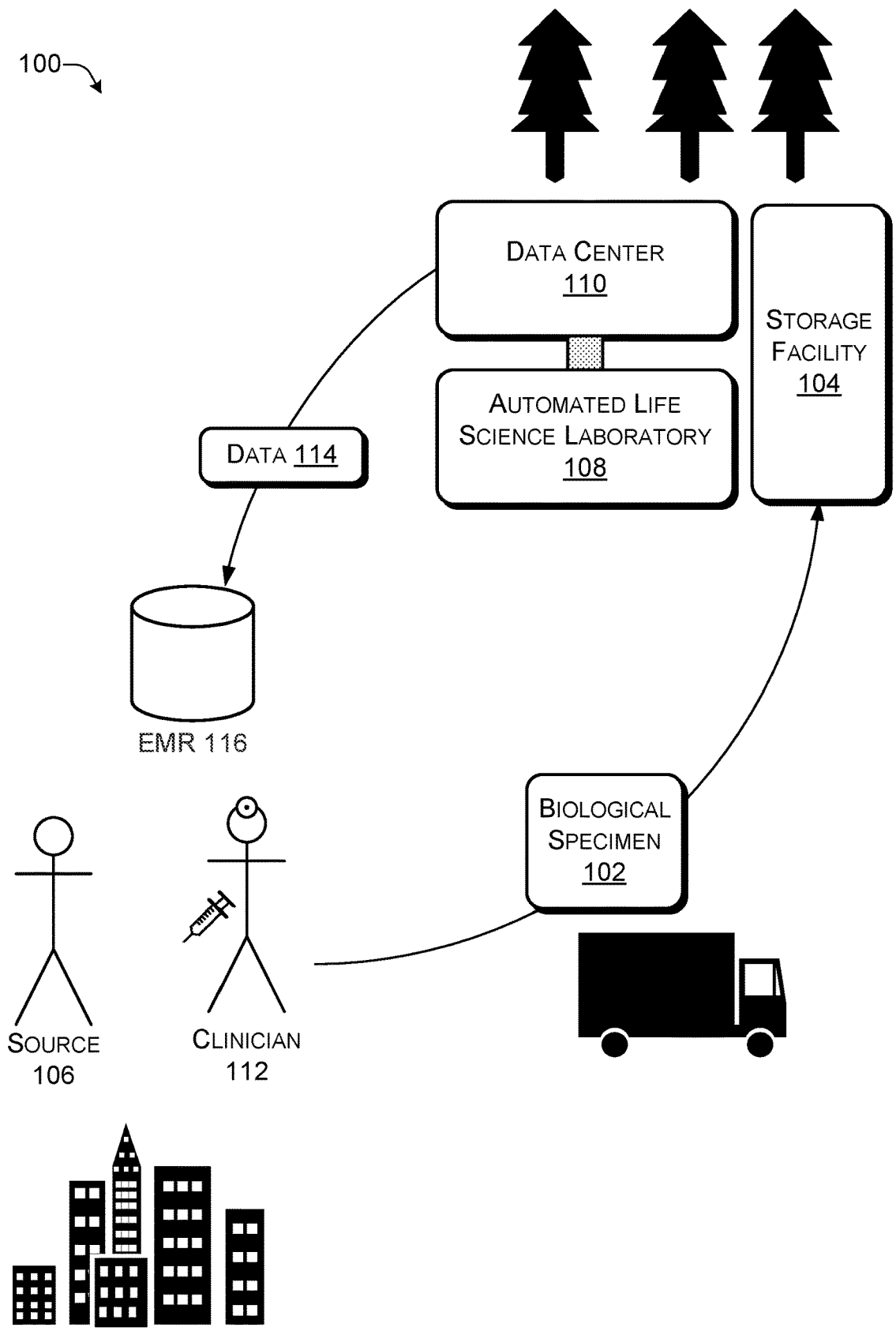
FIG. 1 is a schematic illustrating an automated life science laboratory and a storage facility located with a data center that is situated remote from the place where a biological specimen is obtained.

FIG. 1 shows an illustrative schematic 100 in which a biological specimen 102 is transported to a storage facility 104 that is located remote from a source 106 of the biological specimen 102. Additionally or alternatively, the biological specimen 102 may be transported to an automated life science laboratory 108 that is located together with a data center 110 and/or the storage facility 104. The source 106 of the biological specimen 102 may be a human patient. This illustrative schematic 100 shows a clinician 112 obtaining the biological specimen 102 from the source 106. The source 106 may be a patient who is under the care of a clinician 112 or a healthy individual. The source 106 may also be a nonhuman source such as an animal, plant, fungus, microbe, or other organism. Potential sources 106 are not limited to the examples provided above. The clinician 112 may be a doctor, nurse, phlebotomist, healthcare worker, or the like. Potential types of individuals who could be a clinician 112 are not limited to the examples provided above. The biological specimen 102 may be a blood sample, a tissue sample, or other kind of sample. Examples of blood samples include whole blood, plasma, and serum. Examples of tissue samples include tumor cells, umbilical-cord stem cells, and bone marrow. Examples of other kinds of samples include cerebrospinal fluid, hair, urine, and feces. The possible biological specimens 102 are not limited to the examples provided above.

The biological specimen 102 may be transported to the automated life science laboratory 108 by any conventional means of transport such as a car, truck, motorcycle, train, airplane, helicopter, drone, horse, bicycle, or the like. If it is necessary to maintain the biological specimen 102 at a particular temperature (e.g. refrigerated or frozen), a refrigerated container such as a refrigerated truck or an insulated container including ice, dry ice, or the like may be used. A container for shipping the biological specimen 102 may be standardized for ease of processing. For example, the container may have standard dimensions that allow multiple containers to be efficiently packed together for transport and moved from one mode of transport to another. If the biological specimen 102 is initially collected in a rural location, the biological specimen 102 may be placed a single container at that contained may transported by motorcycle then combined with other containers to fill a truck. In an implementation, the container may be configured to be carried by a drone for rapid transport over relatively short distances.

The storage facility 104 and/or automated life science laboratory 108 may be located together with the data center 110. Both the automated life science laboratory 108 and the data center 110 may be located within the same building, in buildings that are adjoining or adjacent, or in separate buildings on the same plot of land. The location at which the clinician 112 obtains the biological specimen 102 from the source 106 may be remote from the location of the data center 110 and the automated life science laboratory 108. For example, the biological specimen 102 may be obtained an urban area and the automated life science laboratory 108 may be located in a rural area. The distance between the two locations may be "remote" because the distance is greater than about 25 km, greater than about 60 km, greater than about ×100 km, greater than about 500 km, greater than about 1000 km, etc. The distance may also be identified as "remote" due to the length of time necessary to travel between the two locations using conventional mode of transportation in the region. For example, in some regions, the conventional mode of transportation may be a motorized passenger vehicle that can travel approximately 100 km/h but in other regions, the conventional mode of transportation may be walking at a speed of approximately 5 km/h. A "remote" distance may be a distance that is traversed by the conventional mode of transportation in the region been at least about one hour, at least about two hours, at least about three hours, at least about five hours, etc.

Remoteness from the source 106 of the biological specimen 102 and the clinician 112 who obtained the biological specimen 102 may provide the advantages of the land and/or electricity being less expensive. Land and/or electricity is less expensive if it is at least 1% lower cost per the same unit (e.g., square foot, acre, kilowatt hour), moderately less expensive if it is at least 5% lower cost for the same unit, significantly less expensive if it is at least 10% lower cost for the same unit, and substantially less expensive if it is at least 25% lower cost for the same unit.

The storage facility 104 may be considered part of the automated life science laboratory 108 and the biological specimen 102 may be analyzed by a biotechnology protocol at the automated life science laboratory 108. In addition, to be located together with the data center, automated life science laboratory 108 may also interact with the data center. Data generated by performing a biotechnology protocol on the biological specimen 102 may be stored or analyzed by the data center. Data 114 associated with the biological specimen 102 and provided by the data center may be sent to an electronic medical record (EMR) 116. An EMR 116, also referred to as electronic health record (EHR), refers to a systematized collection of patient and population electronically-stored health information in a digital format. EMRs 116 may include a range of data, including demographics, medical history, medication and allergies, immunization status, laboratory test results, gene sequences, radiology images, vital signs, personal statistics like age and weight, and billing information. The data in the EMR 116 may be accessed by the clinician 112 in order to obtain actionable information derived from the biological specimen. Thus, the illustrative schematic shows how about location of an automated life science laboratory 108 (e.g. together with a data center) may be used to achieve efficiencies and cost saving while providing useful data to the clinician 112.

Figure 2:
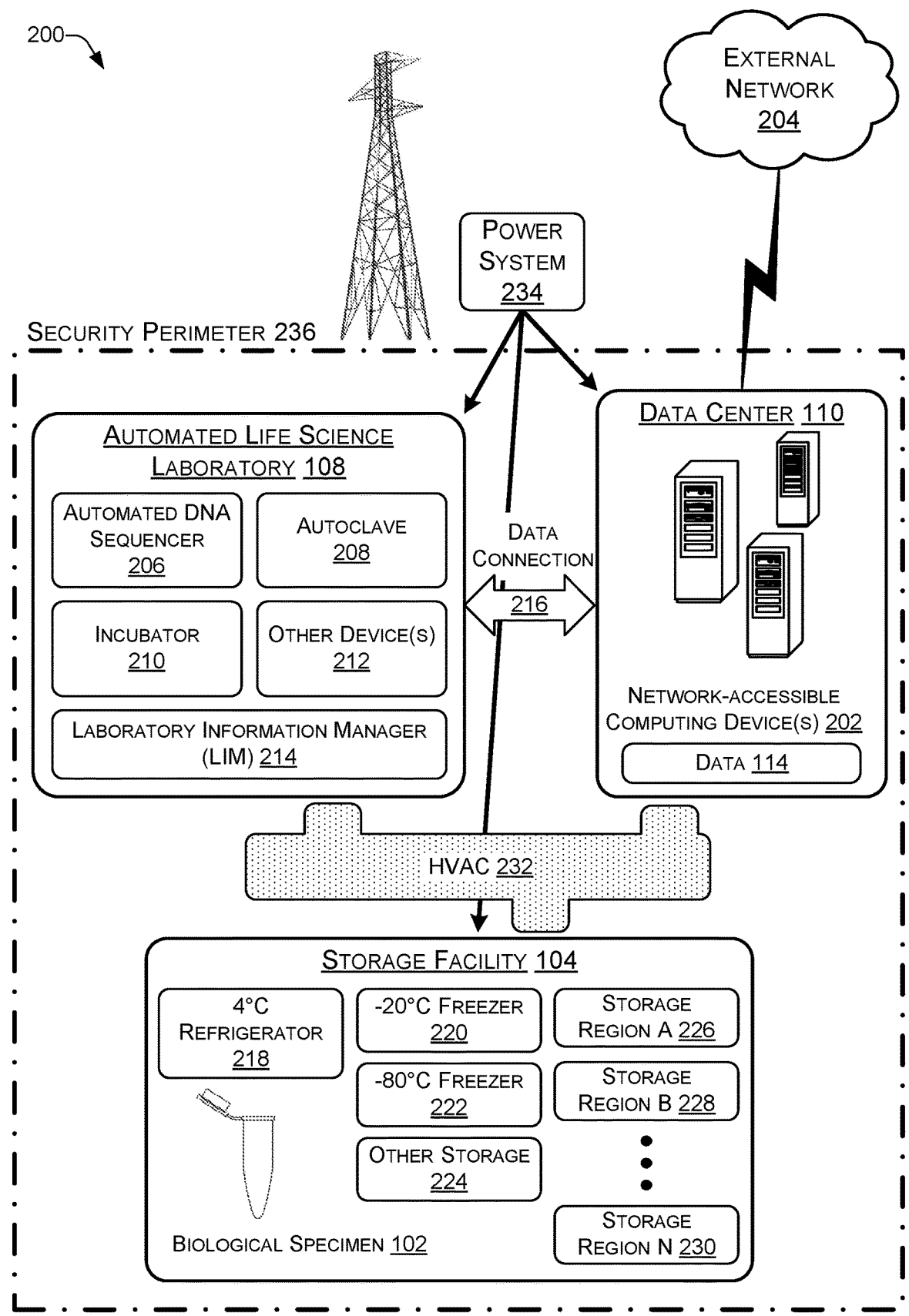
FIG. 2 shows illustrative components of a data center, an automated life science laboratory, and a storage facility.

FIG. 2 shows a block diagram 200 of illustrative components of the data center 110, the automated life science laboratory 108, and a storage facility 104. The data center may include one or more network-accessible computing devices 202 that are connected to an external network 204. The external network 204 may be the Internet or another communications network such as an intranet, a wide area network, a telephone network, etc. The data center 110 is a facility used to house computer systems and associated components, such as telecommunications and storage systems. The data center 110 may include redundant or backup power supplies, redundant data communications connections, environmental controls (e.g., air conditioning, fire suppression), and various security devices.

The network-accessible computing devices 202 may be implemented using one or more types of memory. Memory may include removable storage, non-removable storage, local storage, and/or remote storage to provide storage of computer-readable instructions, data structures, program modules, and other data. The memory may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The network-accessible computing devices 202 may include servers, mainframe computers, storage devices, and the like. For example, the servers may be mounted in rack cabinets (e.g., 19 inch) placed in single rows forming corridors (e.g., aisles) between them. The data center 110 may contain data that is wholly unrelated to the automated life science laboratory 108 or the storage facility 104. It may also contain data 114 associated with the biological specimen. The data 114 may be metadata that describes characteristics are attributes of the biological specimen. Example characteristics may include identity of the source, identity of the specimen, identity of an institution associated with a clinician (e.g., the clinician 112 shown in FIG. 1), a biotechnology protocol used to generate the data, a date and time the data was generated, and the like. Additionally or alternatively, the data 114 may be generated by analysis of the biological specimen 102 such as analysis by a biotechnology protocol.

The automated life science laboratory 108 may include multiple different devices for performing a variety of biotechnology protocols on the biological specimen 102. Some or all of the devices may be configured to implement a biotechnology protocol in an automatic manner that does not require direct and continual human intervention. This may be performed by the use of robotic systems to move biological specimens 102 within the automated life science laboratory 108 and load the biological specimens 102 onto the appropriate device. Many laboratory processes are suited for robotic automation as the processes are composed of repetitive movements (e.g. pick/place, liquid & solid additions, heating/cooling, mixing, shaking, and testing). Examples of robotic suitable for use in an automated life science laboratory 108 include the robot Andrew by Andrew Alliance that is capability of interfacing with conventional volumetric pipettes used by biologists and technical staff. This robotic system, the manual activity of liquid handling can be performed automatically. Plate readers can detect specific biological, chemical or physical events in samples stored in standardized microtiter plates. These plate readers typically use optical and/or computer vision techniques to evaluate the contents of the microtiter plate wells. Of course human intervention may be needed intermittently such as for refilling machines with supplies, reconfiguring robotics to perform new protocols, and troubleshooting errors. However, most of the protocols will be performed without any direct human intervention. This makes large scale automation possible.

The automated life science laboratory 108 may also use a microfluidics system. Microfluidics is a multidisciplinary field intersecting engineering, physics, chemistry, biochemistry, nanotechnology, and biotechnology, with practical applications to the design of systems in which small volumes of fluids will be handled. Typically, fluids are moved, mixed, separated, or otherwise processed. Numerous applications employ passive fluid control techniques like capillary forces. In some applications, external actuation is additionally used for a directed transport of the media. Examples of external actuation include rotary drives applying centrifugal forces for the fluid transport on the passive chips. Active microfluidics refers to the defined manipulation of the working fluid by active (micro) components such as micropumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reducing sample and reagent volumes. Microfluidics systems and methods to divide a bulk volume into partitions include emulsification, generation of "water-in-oil" droplets, and generation of monodisperse droplets as well as using channels, valves, and pumps. Partitioning methods can be augmented with droplet manipulation techniques, including electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components). An implementation of microfluidics systems uses a droplet microactuator. A droplet microactuator can be capable of effecting droplet manipulation and/or operations, such as dispensing, splitting, transporting, merging, mixing, agitating, and the like.

Other techniques for partially or fully automating biotechnology protocols will be understood by those of ordinary skill in the art.

One application for the automated life science laboratory 108 is in genomics. The genomics community is currently collecting millions and eventually billions of blood samples for genomic sequencing. There is a need for efficient sequencing of the deoxyribose nucleic acid (DNA) contained in these blood samples and as sequencing technology improves there will be a need to return to the original blood samples for re-analysis with improved sequencing technology. Thus in an implementation, the automated life science laboratory 108 may include an automated DNA sequencer 206. The automated DNA sequencer 206 can perform the biotechnology protocol of DNA sequencing.

A person having ordinary skill in the art will be aware of multiple techniques currently available for DNA sequencing. One example DNA sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

In addition to the automated DNA sequencer 206, the automated life science laboratory 108 may also include other devices such as autoclave 208 and an incubator 210. An autoclave 208 is a pressure chamber used to carry out industrial processes requiring elevated temperature and pressure different from ambient air pressure. An autoclave 208 may be used to sterilize equipment and supplies by subjecting them to high pressure saturated steam at 121° C. for around 15-20 minutes depending on the size of the load and the contents. An incubator 210 is a device used to grow and maintain microbiological cultures or cell cultures. The incubator 210 maintains optimal temperature (usually 37° C.—human body temperature, for possible pathogens or 25° C. for bacteria from the environment), humidity and other conditions such as the carbon dioxide ($CO_2$) and oxygen content of the atmosphere inside. Incubators are used for experimental work in cell biology, microbiology and molecular biology and are used to culture both bacterial as well as eukaryotic cells.

Both the autoclave and the incubator operate at temperatures higher than typical room temperature. These devices may be assisted in achieving higher temperatures by utilizing waste heat produced by the data center 110. Warmed air may be moved from the data center 110 to the incubator in order to raise the temperature inside incubator and reduce the amount of energy needed to achieve the desired internal temperature. The data center 110 may not create temperatures as high as necessary for use inside of an autoclave, heat from the data center 110 may be used to warm water that is then converted into steam for use in an autoclave. Initial warming of the water using heat from the data center 110 reduces amount of energy necessary to convert the water into steam. Similarly, heat from the data center 110 may be used to heat water prior to feeding the water into a water heater for use as hot water for washing or other purposes. Thus, waste heat from the data center 110 may be used to save energy in the automated life science laboratory 108.

The automated life science laboratory 108 may also include any number of other devices 212 for performing additional biotechnology protocols. The other devices 212 may include, for example, DNA/RNA synthesizers, centrifuges, chromatography columns, microscopes, thermocyclers, mass spectrometers, high-performance liquid chromatographs, a plate reader, etc. Illustrative biotechnology protocols performed by the automated life science laboratory 108 may include DNA sequencing, RNA sequencing, microbiology sequencing, and epigenetic sequencing.

Some or all of the device operations at the automated life science laboratory 108 may be managed by a Laboratory Information Manager (LIM) 214. The LIM 214 is a software-based laboratory and information management system with features that support laboratory operations and controls equipment on a bench top. The LIM 214 can receive instructions and act on those instructions to control devices in the automated life science laboratory 108 such as the automated DNA sequencer 206. In an implementation, the instructions for the LIM 214 may be provided from the data center 110.

Data center 110 and the automated life science laboratory 108 may be connected by a high-capacity data connection 216. The high-capacity data connection may be a direct connection to transmit digital data between the data center 110 and the automated life science laboratory 108 without going through the external network 204. In an implementation, the high-capacity data connection may carry data at a speed of at least about 100 Gb, at least about 250 Gb, or at least about 500 Gb. The high-capacity data connection 216 can be implemented as a two-way connection moving data both from the automated life science laboratory 108 to the data center 110 as well as from the data center 110 to the automated life science laboratory 108. This direct connection between the data center 110 in the automated life science laboratory 108 provides faster transfer of high volumes of data such as genome sequencing data and greater security because the data is not transferred across a publicly-accessible network such as, for example, external network 204.

The storage facility 104 may be implemented as part of the automated life science laboratory 108 or as a separate facility that is present together with the data center 110 in the absence of an automated life science laboratory 108. The storage facility 104 may be configured to store a large number of biological specimens 102. For example, umbilical-cord stem cells may be stored until much later in life when the cells can be used to treat diseases such as Parkinson's disease. Individual specimens may be stored in conditions appropriate for the specimen. For example, cultured eukaryotic cells and bacteria cultures may be stored in a 4° C. refrigerator 218. The 4° C. refrigerator 218 may maintain internal temperatures at or below 4° C., between about 2° C. and 6° C., or between about 0° C. and 4° C. Other materials such as enzymes, PCR products, pelleted bacterial cultures, whole tissue, genomic DNA, and plasmid DNA may be stored in a −20° C. freezer 220. The −20° C. freezer 220 may maintain internal temperatures at or below −20° C., between about −18° C. and −22° C., or between about −18° C. and −40° C. Other specimens such as RNA, whole blood, saliva, sampled cells, and chemically competent $E.\ coli$ may be stored in a −80° C. freezer 222. The −80° C. freezer 222 may maintain internal temperatures at or below −80° C., between about −75° C. and −85° C., or between about −78° C. and −100° C. As mentioned above, the data center 110 may benefit by being located in a cool climate to assist with cooling of the network-accessible computing devices 202. A cool climate will also benefit the storage facility 104 by allowing the cool ambient temperature to maintain cool air surrounding the refrigerators and freezers. Placing the refrigerators and freezers in a relative cool environment, for example at 10° C. rather than at 25° C. room temperature, reduces the amount of energy needed to maintain the 4° C., −20° C., −80° C., etc. temperatures inside of the various refrigerators and freezers.

The storage facility 104 may also include other storage 224 that store biological specimens 102 at various temperatures (e.g., room temperature), various humidity levels, and the like. The storage facility 104 may contain within it any number of multiple storage regions separated into a first storage region, a second storage region, etc. illustrated here by storage region A 226, storage region B 228, . . . , storage region N 230. Each storage region may be implemented as a separate room within the storage facility 104; a separate cabinet within a room; a separate refrigerator; a separate freezer; a separate shelf within a cabinet, within a refrigerator, or within a freezer; a separate rack on a shelf; etc. In an implementation, individual storage regions may be uniquely assigned to separate institutions. For example, there may be multiple freezers that are used only to store biological specimens 102 from a given hospital. Thus, a first storage region may contain only biological specimens 102 from a first location and a second storage region may contain only biological specimens 102 from a second location. However, in an implementation biological specimens 102 from multiple institutions may be stored together and tracked through metadata associated with the biological specimens 102 such as a storage map that identifies the location of each biological specimen 102.

In an implementation, separate storage regions such as storage region A 226 and storage region B 228 may be separated in a way that provides fault tolerance such as, for example separation into two different freezers that are connected to separate electrical connectors on separate circuits. Thus, if storage region A 226 fails to maintain the appropriate temperature it is possible that storage region B 228 will be unaffected.

The data center 110, the automated life science laboratory 108, and the storage facility 104 may share all or part of a heating, ventilation, and air-conditioning (HVAC) system 232. The HVAC system 232 may provide any or all of heating, ventilating, and air-conditioning. The heating system may use any conventional heat source and may in addition, or instead of a conventional heat source, use waste heat from the data center 110 to maintain a desired temperature within the automated life science laboratory 108 and/or the storage facility 104. Thus, heat may be transferred from the data center 110 to the automated life science laboratory 108 and/or the storage facility 104 through the HVAC system 232. Ventilation includes both the exchange of air with the outside as well as circulation of air within the building. Ventilation may be implemented as natural ventilation or as mechanical ventilation. To reduce the risk of contamination, the automated life science laboratory 108 and/or the storage facility 104 may be maintained at a positive pressure to prevent entry of unfiltered, outside air. Air conditioning provides cooling and humidity control. Air conditioning and refrigeration are provided through the removal of heat. Heat can be removed through radiation, convection, or conduction. Refrigeration conduction media such as water, air, ice, and chemicals are referred to as refrigerants. A refrigerant is employed either in a heat pump system in which a compressor is used to drive thermodynamic refrigeration cycle, or in a free cooling system which uses pumps to circulate a cool refrigerant (typically water or a glycol mix). In an implementation, the HVAC system 232 may be integrated with the 4° C. refrigerator 218, −20° C. freezer, and/or −80° C. freezer 222 to provide greater efficiencies through the combination of cooling and refrigeration/freezing.

In addition to a shared HVAC system 232, the data center 110, the automated life science laboratory 108, storage facility 104 may also share a power system 234. The power system 234 may provide a connection to an electrical grid that is shared by the data center 110, the automated life science laboratory 108, and/or the storage facility 104. The shared power system 234 may provide efficiencies through shared equipment that handles potentially large power demands of the data center 110, the automated life science laboratory 108, and the storage facility 104. Additionally, a single connection drawing larger amount of power may allow for increased purchasing leverage and lower prices for electricity. The power system 234 may also provide backup power through generators or batteries that can be shared by all of the data center 110, the automated life science laboratory 108, and the storage facility 104. To prevent single points of failure, all elements of the power system 234, including backup systems, may be fully duplicated. Thus, in this configuration the automated life science laboratory 108 and the storage facility 104 may benefit not only from the lower price of electricity available to the data center 110 but also from the power system 234 that provides redundancy and backup power. Highly reliable power is useful for the storage facility 104 because one role of the storage facility 104 is to maintain the temperature of biological specimens 102 with refrigerators and/or freezers.

The data center 110, the automated life science laboratory 108, and the storage facility 104 may also share a security perimeter 236. The security perimeter 236 may include physical security such as a fencing, protective bollards, mantraps, biometric identification, cameras, motion sensors, security guards, and the like. If the existing security perimeter 236 around a data center 110 includes sufficient unoccupied space, the automated life science laboratory 108 and/or the storage facility 104 may be added without incurring significant additional security costs. Data security is provided by the high-capacity data connection 216 within the security perimeter 236 which allows data to be transferred between the automated life science laboratory 108 and the data center 110 without traveling across a publicly accessible network. Security of the biological specimens 102 is provided by having the automated life science laboratory 108 within the same security perimeter 236 as the storage facility 104 where the biological specimens 102 are stored.

In an implementation the automated life science laboratory 108 and/or the storage facility 104 may be located on a site that is suitable for a data center 110 but does not include a data center 110. For example, if multiple potential sites are identified for building a data center 110 but the data center 110 is built on only one site, then the automated life science laboratory 108 and/or the storage facility 104 may be built on one of the other potential sites (e.g., a second choice site for the data center 110).

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 3:
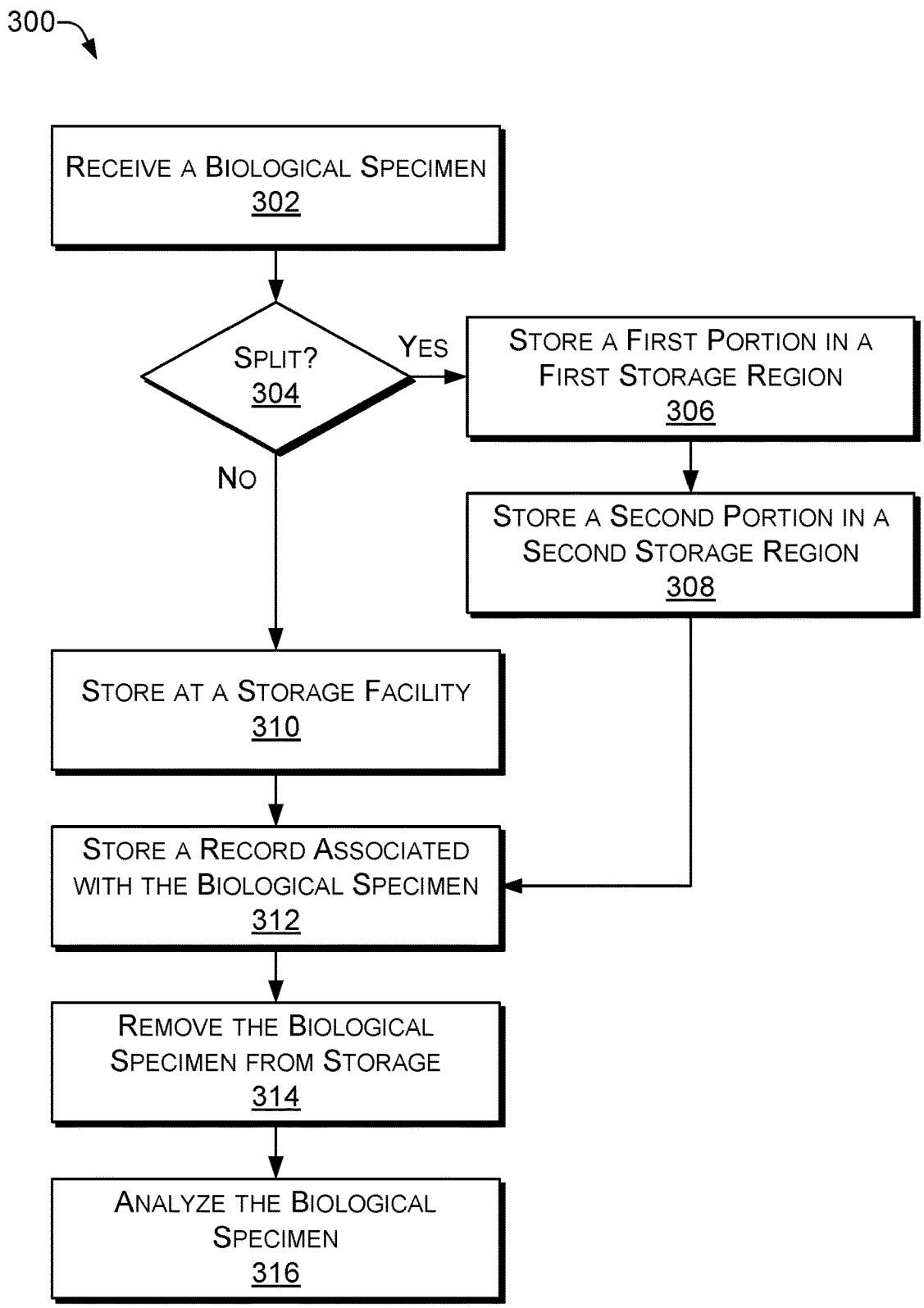
FIG. 3 shows an illustrative process for receiving, storing, and analyzing a biological specimen.

FIG. 3 shows process 300 for receiving, storing, and analyzing a biological specimen 102. Process 300 may be implemented in whole or part by the automated life science laboratory 108, storage facility 104, and the data center shown in FIG. 2.

At 302, the biological specimen 102 is received at the storage facility 104. The biological specimen 102 is collected from a source 106 (e.g., a patient) at a location that is remote from the storage facility 104. For example, the biological specimen 102 may be a blood or tissue specimen collected at a hospital in a city and transported to the storage facility 104 in a rural location.

At 304, it is determined if the biological specimen 102 will be split into two or more different sub-specimens. The decision to split the biological specimen 102 may be based on a volume or weight of the biological specimen 102. Additionally or alternatively, the decision to split the biological specimen 102 may be based on comparison of an amount of the biological specimen 102 needed to perform a biotechnology protocol with a total amount of the biological specimen. If the biological specimen 102 is split, process 300 follows the "yes" path. If the biological specimen 102 is not split, process 300 follows the "no" path.

At 306, a first portion of the biological specimen 102 is stored in a first region of the storage facility 104 such as storage region A 226. The first region of the storage facility 104 may be any discrete and identifiable area such as a room, a cabinet, a refrigerator, a freezer, a shelf, a rack, a box, etc.

At 308, a second portion of the biological specimen 102 is stored in a second region of the storage facility 104 such as storage region B 228. The first portion and the second portion of the biological specimen 102 may be stored under identical or different conditions. For example, the first portion may be placed in an −80° C. freezer 222 for long-term storage and the second portion may be placed in a 4° C. refrigerator 218 for short-term storage. In an implementation, the biological specimen 102 may be split shortly after collection while still at or near the location of collection then the first portion and the second portion may be sent to different storage facilities remote from each other.

At 310, if the biological specimen 102 is not split, it is stored at the storage facility 104. For example, the biological specimen 102 may be stored in the 4° C. refrigerator 218, the −20° C. freezer 220, the −80° C. freezer 222, or the other storage 224. The storage facility 104 may be located on a same site as the data center 110. As described above, the data center 110 includes a plurality of network-accessible computing devices 202 (e.g., servers) connected to an external network 204 such as the Internet. The same "site" may be the same plot or parcel of land as identified by real-estate records, a location within a shared security perimeter 236, a location that shares at least part of an HVAC system 232, or a location that shares at least part of a power system 234. Land and/or electricity are less expensive at the site than at the location where the biological specimen 102 is obtained from the source 106.

At 312, a record containing data 114 associated with the biological specimen 102 is stored in the data center 110. The data 114 may be metadata describing the biological specimen 102 or data 114 generated by performing a biotechnology protocol on the biological specimen 102. Records in the data center 110 may be stored in specific locations or on specific networks-accessible computing devices 202 based on the location where the biological specimen 102 was collected. For example, if the location is a hospital, records for biological specimens 102 from the hospital may be stored on a particular storage device that is used only for records from that hospital. A second storage device may be used for storing records from other biological specimens 102 that were collected at a second location such as a different hospital. Similarly, if the network-accessible computing devices 202 in the data center 110 are used for processing and analyzing the data 114 associated with the biological specimens 102, a network-accessible computing device 202 (e.g., a server) may be used only for work associated with a specific location.

At 314, at least a portion of the biological specimen 102 is removed from storage at the storage facility 104 (e.g., so that a biotechnology protocol may be performed on the biological specimen 102). The biological specimen 102 may be removed by a robot or other automated handling technology. A determination performed at the data center 110 may cause removal of the biological specimen 102 from storage. The determination may be based on the processing of a command sent from outside of the automated life science laboratory 108 or the storage facility 104. For example, a person at a different location may request that biological specimen 102 be pulled from storage and the determination may be a determination that a unique identifier for the requested biological specimen 102 match the identifier associated with a particular specimen in storage. The determination may also be based on a computation performed at the data center 110 such as determining a volume of the remaining biological specimen 102, an amount of elapsed time, analysis of data from a separate biological specimen 102, or the like. In an implementation, instructions to remove the biological specimen 102 from storage may be sent from the data center 110 to the LIM 214 in the automated life science laboratory 108 which in turn communicates instructions to automated handling equipment in the storage facility 104 and/or the automated life science laboratory 108.

At 316, the biological specimen 102 is analyzed by a biotechnology protocol at the automated life science laboratory 108. The biotechnology protocol may be any biotechnology protocol including the biotechnology protocols discussed above.

Figure 4:
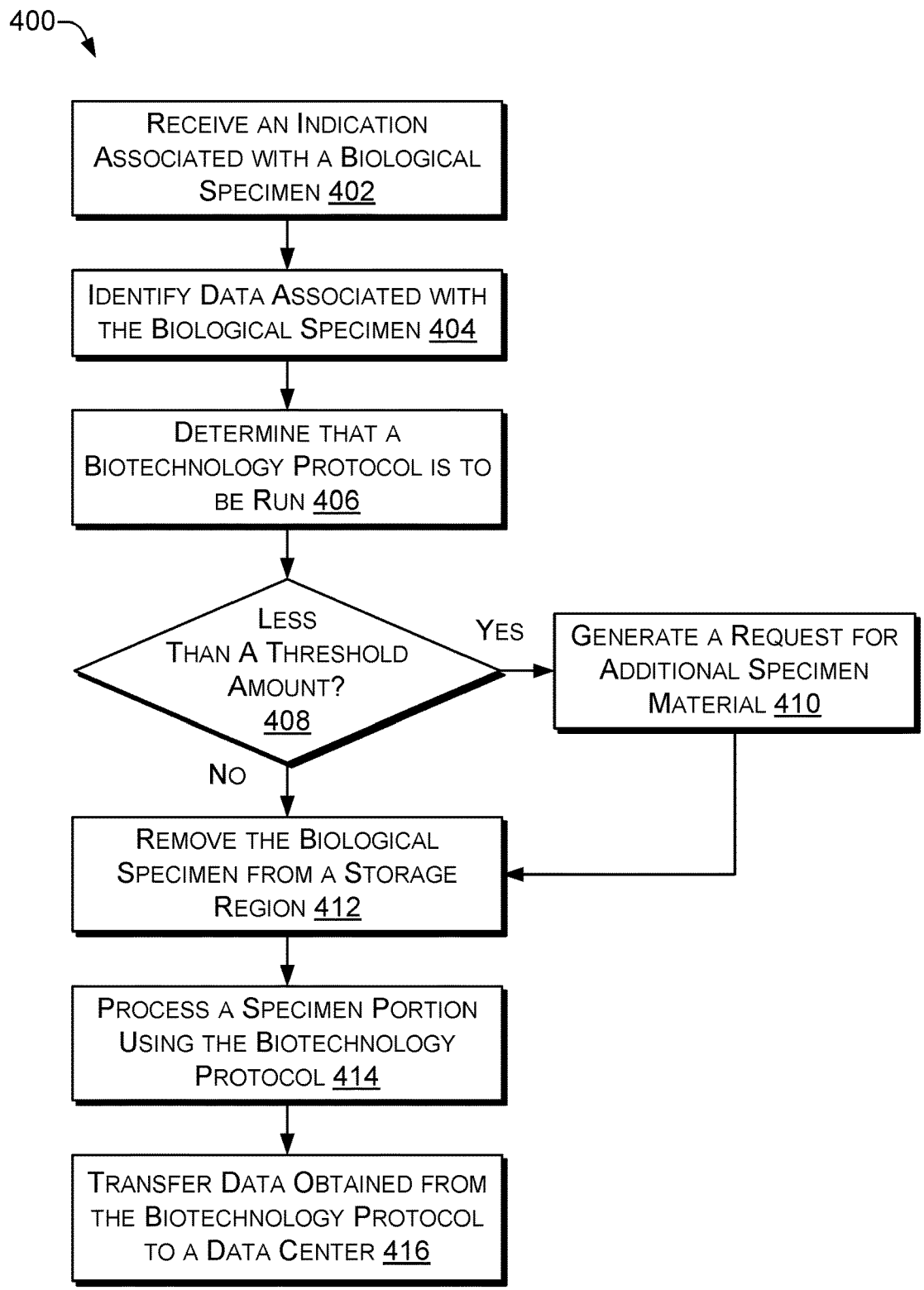
FIG. 4 shows an illustrative process for determining a biotechnology protocol to run on a biological specimen and transferring data obtained from the biotechnology protocol to a data center.

FIG. 4 shows process 400 for determining a biotechnology protocol to run on a biological specimen 102 and transferring data obtained from the biotechnology protocol to a data center 110.

At 402, an indication associated with a biological specimen 102 is received via a network. The network may be the external network 204 shown in FIG. 2. The indication may be generated by a person such as, but not limited to, the clinician 112 who obtained the biological specimen 102. For example, the indication may be instructions to submit the biological specimen 102 for processing using the biotechnology protocol. This implementation may allow the clinician 112 to remotely order analysis of the biological specimen 102 and have that analysis performed in the automated life sciences laboratory 108 without direct, continual human intervention. The clinician 112 may order the analysis by entering instructions into the EMR 116.

In an implementation, the indication may indicate that a count-down timer has reached zero. For example, a biological specimen 102 may be analyzed repeatedly at a defined frequency such as every six months, every year, every five years, etc. When the timer finishes counting down the indication is generated and the timer may rest to begin counting down again.

The indication may also be an indication that a first biotechnology protocol used to generate the data associated with the biological specimen 102 has changed (e.g., become outdated). For example, if the data is gene sequence data and the technology for DNA sequencing has changed, the availability of new gene sequencing technology may trigger generation of the indication. Other changes that could result in generating the indication include new research findings that suggest a different way to analyze existing biological specimens 102.

The indication may identify one or more biological specimens 102 and provide instructions for an operation to perform on the biological specimen(s) 102. For example, the indication may indicate all biological specimens 102 for which the gene sequence data was generated using a no-longer-current DNA sequencing technology. In an implementation, the indication may be provided to the LIM 214 for implementation by the automated life science laboratory 108.

At 404, data associated with the biological specimen 102 is identified. The data may be identified due to a unique identifier (e.g., a globally unique identifier "GUID") shared by the data and the biological specimen. In an implementation, the data may be the data 114 stored in the data center 110.

At 406, a determination is made to run a biotechnology protocol on the biological specimen 102. The determination may be based at least in part on the indication received at 402. For example, if the indication is instructions to perform a biotechnology protocol on the biological specimen 102, then it will be determined to run the requested biotechnology protocol.

In an implementation, the determination may include decision analytics that considers if it more valuable to consume a portion of the biological specimen 102 now and obtain information through analysis or if it more valuable to save the biological specimen 102 for later. When the biological specimen 102 is from a patient, the decision analytics may consider clinical outcomes for similar patients over the remainder of their lifespans and how data obtained from the biological sample 102 may improve the clinical outcomes. The decision analytics may be performed by one or more of the network-accessible computing devices 202 in the data center 110. Thus, a determination by the decision analytics that consuming a portion of the biological specimen 102 now will generate the best outcome may be the determination that a biotechnology protocol is to be run on the biological specimen 102.

At 408, it is determined if less than a threshold amount of the biological specimen 102 remains in a storage region (e.g. storage region A 226). If there is less than the threshold amount of the biological specimen 102 remaining in the storage region, process 400 follows the "yes" path. If there is equal to or more than the threshold amount of the biological specimen 102 remaining, then process 400 follows the "no" path. The threshold amount may be based on volume, weight, or other metric suitable for evaluating an amount of the biological specimen 102. The threshold amount may be set arbitrarily, some possible settings include an amount of biological specimen 102 that is consumed by performing one biotechnology protocol and an amount of biological specimen 102 that expected to be consumed during a time period (e.g., one year).

At 410, when less than the threshold amount of the biological specimen 102 remains, a request is generated for additional specimen material. The request is for the same material that comprises the original biological specimen 102. For example, if the biological specimen 102 is whole blood then the request is for more whole blood. In an implementation, the request may be sent to the EMR 116 through which the clinician 112 or other person is informed of the need to collect another biological specimen 102 from the source 106. If the source 106 is a person, the notification may be sent directly to the source 106 asking him or her to provide another biological specimen 102.

At 412, if it is determined that at least the threshold amount of the biological specimen 102 remains, at least a portion of the biological specimen 102 is removed from the storage region to obtain a specimen portion. The specimen portion may be the entire biological specimen 102 or less than the entire amount.

At 414, the specimen portion is processed using the biotechnology protocol that was determined at 406. For some biotechnology protocols, processing the specimen portion consumes the specimen portion. Results of the biotechnology protocol are captured as data such as a sequence of nucleotide bases, an image, presence (or absence) of an interaction, etc.

At 416, the data obtained from the biotechnology protocol is transferred from a device for performing the biotechnology protocol to the data center 110. The data may be transferred through the high-capacity data connection 216 without passing through the external network 204. Once at the data center 110, the data may be stored as data 114.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Throughout these example clauses, parenthetical remarks are examples and are not limiting. Examples given in the parenthetical remarks of specific example clauses can also apply to the same terms appearing elsewhere in these example clauses.

Clause 1. A system comprising:

an automated life science laboratory configured to implement at least one biotechnology protocol without direct, continual human intervention (e.g., automatically);

a data center comprising a plurality of network-accessible computing devices connected to an external network; and a high-capacity data connection configured to carry data from the automated life science laboratory to the data center without passing through the external network.

Clause 2. The system of clause 1, further comprising a storage facility configured to store a plurality of biological specimens, the biological specimens in the storage facility being accessible by the automated life science laboratory without direct human intervention.

Clause 3. The system of any of clauses 1 or 2, further comprising a heating, ventilation, and air-conditioning (HVAC) system shared at least in part by the automated life science laboratory and the data center.

Clause 4. The system of any of clauses 1 or 2, further comprising an air-conditioning system shared at least in part by the automated life science laboratory and the data center.

Clause 5. The system of any of clauses 1-4, further comprising a connection to an electricity grid shared by the automated life science laboratory and the datacenter.

Clause 6. The system of any of clauses 1-5, further comprising a security perimeter shared at least in part by the automated life science laboratory and the data center.

Clause 7. The system of any of clauses 1-6, wherein the automated life science laboratory comprises at least one automated deoxyribose nucleic acid (DNA) sequencer and the at least one biotechnology protocol comprises DNA sequencing.

Clause 8. The system of any of clauses 1-7, wherein data center comprises data generated from the at least one biotechnology protocol, the data transferred to the data center from the automated life science laboratory via the high-capacity data connection.

Clause 9. The system of any of clauses 1-8, further comprising a Laboratory Information Manager (LIM) configured to receive instructions from the data center for controlling at least a portion of the automated life science laboratory.

Clause 10. A method comprising:
receiving a biological specimen at a storage facility, the biological specimen collected from a source at a location that is remote from the storage facility; and
storing the biological specimen at the storage facility, the storage facility located on a same site as a data center comprising a plurality of network-accessible computing devices connected to an external network, land and electricity at the site being less expensive than land and electricity at the location.

Clause 11. The method of clause 10, wherein the biological specimen comprises a blood or tissue specimen and storing the biological specimen comprises placing the specimen in a −20° C. freezer or in a −80° C. freezer.

Clause 12. The method of any of clauses 10 or 11, wherein the storage facility comprises a first storage region containing only biological specimens from the location and a second storage region containing only biological specimens from a second location.

Clause 13. The method of any of clauses 10-12, further comprising storing a record containing data associated with the biological specimen in the data center.

Clause 14. The method of clause 13, wherein the data center comprises a first network-accessible computing device storing only data associated with biological specimens from the location and a second network-accessible computing device storing only data associated with biological specimens from a second location.

Clause 15. The method of any of clauses 10-14, further comprising splitting the specimen into a first portion and a second portion, storing the first portion at a first storage region within the storage facility, and storing the second portion within a second storage region within the storage facility.

Clause 16. The method of any of clauses 10-15, further comprising, responsive to a determination (e.g., external command to pull a biological specimen; decision that a biological specimen is to be (re)tested based on a factor) performed at least in part at the data center, removing at least a portion of the biological specimen from storage at the storage facility.

Clause 17. A method comprising:
receiving, via an external network, an indication (e.g., provide by a LIM) associated with a biological specimen;
identifying data associated with the biological specimen;
determining (e.g., based at least in part on the indication) that a biotechnology protocol is to be run on the biological specimen;
removing (e.g., based at least in part on the determining) at least a portion of the biological specimen from a storage region to obtain a specimen portion; and
processing the specimen portion using the biotechnology protocol without direct human intervention.

Clause 18. The method of clause 17, wherein:
the indication comprises an indication that a first biotechnology protocol (e.g., old protocol) associated with generation of the data associated with the biological specimen has changed, and
the biotechnology protocol comprises a second biotechnology protocol (e.g., new protocol), the second biotechnology protocol being different from the first biotechnology protocol and obtaining analogous data as the first biotechnology protocol (wherein the second biotechnology protocol is performed on all biological specimens for which the associated data was generated by the first biotechnology protocol).

Clause 19. The method of any of clauses 17 or 18, wherein the indication comprises instructions to submit the specimen for processing using the biotechnology protocol without direct human intervention (e.g., automatically).

Clause 20. The method of any of clauses 17-19, further comprising determining that less than a threshold amount of the biological specimen remains in the storage region.

Clause. 21. The method of clause 20, further comprising generating a request (at least partially responsive to the determining) to obtain an additional biological specimen of the same material from the same source as the biological specimen.

Clause 22. The method of clause 21, further comprising sending the request to an electronic medical record (EMR) system.

Clause 23. The method of any of clauses 17-22, further comprising transferring (metadata associated with the biological sample and) data obtained from the biotechnology protocol from a device for performing at least a portion of the biotechnology protocol to a data center via a high-capacity data connection without passing through the external network.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The invention claimed is:
1. A system comprising:
an automated life science laboratory comprising a robotic system configured to implement at least one biotechnology protocol, wherein the robotic system comprises an automated deoxyribose nucleic acid (DNA) sequencer that implements a biotechnology protocol of the at least one biotechnology protocol and a plate reader that implements a computer vision technique for evaluating a result of the biotechnology protocol, wherein the robotic system carries out most of the at least one biotechnology protocol and human intervention with the automated life science laboratory includes refilling machines with supplies, reconfiguring the robotic system to perform new protocols, and troubleshooting errors;
a data center comprising a plurality of network-accessible computing devices connected to the plate reader, the DNA sequencer, and an external network, wherein the plurality of network-accessible computing devices are programmed to provide, to the automated life science laboratory, instructions for controlling the DNA sequencer and the plate reader of the robotic system; and
a data connection configured to carry data from the automated life science laboratory to the data center by directly connecting the automated life science laboratory with the data center.
2. The system of claim 1, further comprising a storage facility storing a plurality of biological specimens, wherein the robotic system from the automated life science laboratory accesses the biological specimens in the storage facility without direct human intervention, and wherein human intervention is used to place the biological specimens into the storage facility.

3. The system of claim 1, further comprising a heating, ventilation, and air-conditioning (HVAC) system shared at least in part by the automated life science laboratory and the data center.

4. The system of claim 1, further comprising a security perimeter that surrounds the automated life science laboratory and the data center, wherein the security perimeter prevents unauthorized access to the automated life science laboratory and the data center including one or more of: fencing, protective bollards, mantraps, biometric identification, cameras, and motion sensors.

5. The system of claim 1, wherein the automated life science laboratory comprises at least one automated deoxyribose nucleic acid (DNA) sequencer and the at least one biotechnology protocol comprises DNA sequencing.

6. The system of claim 1, wherein the data center stores data generated from the at least one biotechnology protocol, and wherein the data is transferred to the data center from the automated life science laboratory via the data connection.

* * * * *